US011571373B2

(12) United States Patent
Avshalomov

(10) Patent No.: US 11,571,373 B2
(45) Date of Patent: Feb. 7, 2023

(54) SKIN CARE PREPARATIONS FOR BABIES

(71) Applicant: Mattityahu Avshalomov, Ramat Gan (IL)

(72) Inventor: Mattityahu Avshalomov, Ramat Gan (IL)

( * ) Notice: Subject to any disclaimer, the term of this patent is extended or adjusted under 35 U.S.C. 154(b) by 362 days.

(21) Appl. No.: 16/062,194

(22) PCT Filed: Dec. 18, 2016

(86) PCT No.: PCT/IL2016/051352
§ 371 (c)(1),
(2) Date: Jun. 14, 2018

(87) PCT Pub. No.: WO2017/103936
PCT Pub. Date: Jun. 22, 2017

(65) Prior Publication Data
US 2018/0369091 A1 Dec. 27, 2018

Related U.S. Application Data

(60) Provisional application No. 62/267,931, filed on Dec. 16, 2015.

(51) Int. Cl.
| | |
|---|---|
| *A61K 8/365* | (2006.01) |
| *A61K 8/27* | (2006.01) |
| *A61K 8/44* | (2006.01) |
| *A61Q 19/00* | (2006.01) |
| *A61K 36/02* | (2006.01) |
| *A61K 8/19* | (2006.01) |
| *A61K 36/185* | (2006.01) |
| *A61K 36/48* | (2006.01) |
| *A61K 36/28* | (2006.01) |
| *A61K 8/9789* | (2017.01) |
| *A61K 8/9794* | (2017.01) |
| *A61K 8/34* | (2006.01) |
| *A61K 8/36* | (2006.01) |
| *A61K 8/37* | (2006.01) |
| *A61K 8/39* | (2006.01) |
| *A61K 8/46* | (2006.01) |
| *A61K 8/891* | (2006.01) |
| *A61K 8/92* | (2006.01) |

(52) U.S. Cl.
CPC .............. *A61K 8/365* (2013.01); *A61K 8/19* (2013.01); *A61K 8/27* (2013.01); *A61K 8/342* (2013.01); *A61K 8/345* (2013.01); *A61K 8/361* (2013.01); *A61K 8/37* (2013.01); *A61K 8/39* (2013.01); *A61K 8/44* (2013.01); *A61K 8/466* (2013.01); *A61K 8/891* (2013.01); *A61K 8/922* (2013.01); *A61K 8/9789* (2017.08); *A61K 8/9794* (2017.08); *A61K 36/02* (2013.01); *A61K 36/185* (2013.01); *A61K 36/28* (2013.01); *A61K 36/48* (2013.01); *A61Q 19/005* (2013.01); *A61K 2800/805* (2013.01)

(58) Field of Classification Search
None
See application file for complete search history.

(56) References Cited

U.S. PATENT DOCUMENTS

| | | | | |
|---|---|---|---|---|
| 2007/0187429 A1* | 8/2007 | Farahmand | ............ | B65D 35/22 222/94 |
| 2009/0269419 A1* | 10/2009 | Pierrisnard | .............. | A61K 8/19 424/638 |
| 2009/0324705 A1* | 12/2009 | Vikhrieva | ................ | A61K 9/06 424/450 |
| 2012/0282194 A1* | 11/2012 | Florence | ................ | A61K 9/107 424/59 |

FOREIGN PATENT DOCUMENTS

| | | |
|---|---|---|
| CN | 101129324 A | 2/2008 |
| CN | 104173213 | 12/2014 |
| CN | 104958218 A | 10/2015 |
| WO | 03043596 A2 | 5/2003 |
| WO | 2007078056 A1 | 7/2007 |

OTHER PUBLICATIONS

"O8 Oeight—Baby Diaper Rash Cream Ointment 4 oz natural", Retrieved from Internet on Oct. 2, 2018 <http://www.o8shop.com/product/diaper-rash-cream/?v=7516fd43adaa>.
"08 Oeight—Premium Gift Pack Box for Baby skin care: Baby Shampoo/ Baby lotion/ diaper rash cream set", Retrieved from Internet on Oct. 2, 2018 <http:/www.o8shop.com/product/baby-gift-pack/?v=7516fd43adaa>.
"Premium Gift Pack Box for Baby Skin Care: Baby Shampoo/baby Lotion/diaper Rash Cream Set"; Review on Oct. 11, 2015 <https://www.amazon.com/O8-Oeight-Premium-Shampoo-Lotion/dp/B015JKRBXO>.
International Searching Authority PCT/IL2016/051352 Completed Mar. 16, 2017; dated Mar. 19, 2017 6 pages.
Written Opinion of the International Searching Authority PCT/IL2016/051352 dated Mar. 19, 2017 10 pages.

* cited by examiner

*Primary Examiner* — David J Blanchard
*Assistant Examiner* — Sarah J Chickos
(74) *Attorney, Agent, or Firm* — Mark M. Friedman

(57) ABSTRACT

The present invention provides a skin care preparation for babies, comprising: pharma grade water; at least one stabilizer; at least one nutrient; at least one emulsifier; wherein said preparation further comprises Zinc gluconate & magnesium asparate & copper gluconate ("SEPITONIC™-M3") and *Dunaliella salina* extract.

1 Claim, No Drawings

SKIN CARE PREPARATIONS FOR BABIES

RELATED APPLICATIONS

This application is a National Phase of PCT Patent Application No. PCT/IL2016/051352 having International filing date of Dec. 18, 2016, which claims the benefit of priority of U.S. Provisional Application No. 62/267,931 filed on Dec. 16, 2015 entitled SKIN CARE PREPARATIONS FOR BABIES. The contents of the above applications are all incorporated by reference as if fully set forth herein in their entirety.

FIELD OF THE INVENTION

The present invention is directed towards skin care compositions and processes for preparing and using the same. More specifically, the present invention relates to skin care compositions for babies comprising ingredients integrated into a single complex having unique properties for enhancing skin's immunity and efficacy against environmental and internal damage.

BACKGROUND OF THE INVENTION

When babies are born, they emerge from the womb's sterile environment into a world filled with bacteria, pollution, humidity and heat, solar radiation, etc. Baby's skin excels in its ability to adapt to the environment. This ability improves gradually over the first years of life, in general, and during the first year, in particular. This period is marked by adaptation to human contact and to open air, at home and outside. Together with this, the baby's diet (either mother's milk or formula) are filled with hormones which often intensify the activity of sebaceous glands, etc.

During this adaptation period, a large percentage of babies suffer from various skin disorders. Recognizing and taking care of them is essential for easy, quick and "painless" adaptation.

Patent application CN104398446A discloses a universal baby skin care and a preparation thereof. The universal baby skin care is prepared from the following components in parts by weight: 0.03-3 parts of a witch hazel extract, 0.02-2 parts of a lithospermum extract, 0.03-2 parts of a red current extract, 2-4 parts of wool fat, 1-3 parts of Vaseline, 5-7 parts of glycerin monostearate, 4-8 parts of glycerinum, 0.02-1 part of lavender essence, 0.3-3 parts of lecithin, 0.3-0.5 part of triethanolamine, 3-5 parts of propylene glycol, 0.02-5 parts of alcohol and the balance of deionized water. Since the witch hazel extract, the lithospermum extract and the red current extract are contained, the universal baby skin care can be used for diminishing inflammation and relieving the irritated skin, and dry skin is prevented; furthermore, the effect of curing a wound is achieved. By mixing of other auxiliary agents in the skin care, an extremely good working effect can be achieved in a use process.

Patent CN101229109 discloses a skin-protecting product suitable for the skin characteristics of a baby of 7 to 12 months, which adds a natural concentrated Chinese witch-hazel extract, an oat extractive with the efficacies of anti-simulation and anti-hypersusceptibility, and a rice embryo oil with nutrition efficacy into a cosmetic to complement the immanent water and nutrition of the skin at the same time of enhancing the self-external counterirritant capacity and barrier action of the baby skin through a cooperated synergy; thereby enhancing the skin immunity capacity of the baby skin, preventing the baby skin problem and leading the skin to be more healthy and lenitive.

Patent U.S. Pat. No. 6,589,537 discloses a resistant to body fluids, organic oil-based topical transdermal composition for the alleviation and treatment of infant skin conditions, including, dry, sensitive, chapped, cracked, itching reddened, and flaking skin, as well as infant skin infirmities associated with eczema, dermatitis, and diaper rash, which has as main constituents, organic oil lipids, vitamin A, tocopheral linoleate, and tincture of benzoin, in an organic beeswax emulsifying base.

Patent application CN101732222 discloses an embrocation for treating infant diaper rash, which is prepared from the following raw materials in percentage by weight: 15 to 18 percent of glyceryl monostearate, 4 to 6 percent of caprylic acid triglyceride, 2 to 4 percent of vaseline, 1 to 3 percent of lanoline, 1 to 2 percent of spermol, 1 to 2 percent of lanonol polyoxyethylene ether acetylated ester, 0.1 to 0.3 percent of allantoin, 4 to 6 percent of propylene glycol and 60 to 70 percent of deionized water. The embrocation is prepared by adding the allantoin and the propylene glycol into water; heating the mixture to 75 DEG C. for later use; mixing the rest components, and then heating to 75 DEG C.; dissolving the components, and mixing the dissolved mixture and the liquid for later use; continuously stirring the mixture; adding appropriate amount of essence when forming a paste; and uniformly stirring the mixture to obtain the embrocation. Compared with the prior art, the embrocation has modest property, good effects of diminishing inflammation, relieving itching and sterilizing, and obvious effects on the infant diaper rash.

Patent U.S. Pat. No. 6,248,340 discloses a composition useful for care of skin conditions and for skin protection and to a method for its preparation. The present invention further relates to a method for skin care and protection using said composition. More specifically, the present invention relates to a composition combining plant and algae extracts with water solutions from the Dead Sea especially useful for treating skin wrinkles and retaining skin moisture, to a method for the preparation thereof and to a method for skin care and protection comprising application of said composition.

Patent application WO2007078056 discloses a cosmetic composition for improving skin complexion comprising an alga extract. More particularly, the cosmetic composition according to the present invention comprises an extract from the alga *Dunaliella Salina* to provide energy to skin cells and promotes turn-over of epidermal cells, thereby providing skin complexion and clearness improving effect on the aged skin or darkened skin caused by outer circumstance and stress.

Patent application CN104771352 discloses a cushion BB cream and preparation method. The cushion BB cream comprising the following components: polybutylene, cyclopentasiloxane polydimethylsiloxanes, glycerin, tridecanol stearate, titanium dioxide, PEG-10 dimethicone, methoxy ethylhexyl acrylate, distearyl dimethyl ammonium hectorite, polydimethylsiloxane, sunflower extract, mica, coconut oil, Tahitian *gardenia*, tocopherol, sodium chloride, Portugal glycans, folic acid, lactic acid bacteria or fermented soybean product extract, phenoxyethanol, hydrogenated polydecene, *Dunaliella* algae extract, ethylhexylglycerin, bismuth oxychloride, iron oxide yellow, red iron oxide yellow, light fruit licorice extract, water. The preparation method is a component of every Canadian should stir until mixture is dissolved, along with the next component. Cushion BB cream of the invention enables the skin to improve skin moist, tender and delicate, hidden pores, even skin tone, blemishes modification, anti-sweat makeup better hold multiple effects.

Patent application WO2008104570 discloses a formulation for use in cosmetic preparations which contain plant extracts, which comprises a component for enhancing the activity of plant extracts or booster, cell turnover and metabolism accelerator, and optionally excipients which are acceptable from a cosmetic standpoint, the enhancing component comprising one or more vitamins or fatty acids which are components of vitamins and zinc or zinc salts or biomineral complexes based on zinc or other forms of zinc which are biologically active and cosmetically acceptable.

SUMMARY OF THE INVENTION

It is one object of the present invention to provide a skin care preparation for babies, comprising: pharma grade water; at least one stabilizer; at least one nutrient; at least one emulsifier; wherein said preparation further comprises Zinc gluconate & magnesium asparate & copper gluconate ("SEPITONIC™-M3") and *Dunaliella salina* extract.

It is another object of the present invention to provide a preparation where said at least one stabilizer is selected from a group consisting of: Stearic acid; *Butyrospermum parkii* (shea butter); *Cera alba* (beeswax); Glycerin; Phenoxyethanol; Sodium hydroxide; Carbomer (benzene free); Perfume 187722 creme soap; *Chamomilla recutita (matricaria)* extract, Sodium chloride; Citric acid; Zinc oxide (ci 77947); Caprylic/capric triglyceride; Hydroxypropyl Guar Hydroxypropyltrimonum Chloride; Ethylhexylglycerin; and any combination thereof.

It is another object of the present invention to provide a preparation where said at least one nutrient is selected from a group consisting of Panthenol; Tocopheryl acetate; *Olea europaea* (olive) fruit oil; Aloe barbadensis (aloe vera leaf juice); Allantoin; Sodium Cocoamphoacetate; Disodium Laureth Sulfosuccinate; Aloe Barbadensis Leaf Juice; Zinc oxide (ci 77947); *Ricinus communis* (castor) seed oil; Panthenol; Gluconolactone & sodium benzoate & calcium gluconate; Aqua & sodium lactate & sodium pca & glycine & fructose & urea & niacinamide & inositol & sodium; Benzoate; and any combination thereof.

It is another object of the present invention to provide a preparation where said at least one emulsifier is selected from a group consisting of Stearic acid; *Butyrospermum parkii* (shea butter); Dimethicone; Cetearyl alcohol; Glycerin; Panthenol; *Olea europaea* (olive) fruit oil; Carbomer (benzene free); Sodium Cocoamphoacetate; Disodium Laureth Sulfosuccinate; *Chamomilla Recutita* Flower Water; *Olea europaea* (olive) Husk oil; Ethylhexylglycerin; Cetearyl alcohol & peg-20 stearate; *Ricinus communis* (castor) seed oil; Caprylic/capric triglyceride; Polysorbate 60; Dimethicone; *Calendula officinalis* flower extract (marigold oil); Magnesium laureth sulfate & disodium laureth sulfosuccinate; Cocamidopropyl betaine & aqua; and any combination thereof.

It is another object of the present invention to provide a preparation where said preparation is formulated as a pharmaceutically acceptable Baby lotion.

It is another object of the present invention to provide a preparation where said preparation is formulated as a pharmaceutically acceptable Baby cleansing mousse.

It is another object of the present invention to provide a preparation where said preparation is formulated as a pharmaceutically acceptable Dipper rash cream.

It is another object of the present invention to provide a preparation where said preparation is formulated as a pharmaceutically acceptable Tearless Baby Shampoo.

It is another object of the present invention to provide a skin care preparation for babies, comprising: *Persea Gratissima* Avocado Oil, *Simmondsia Chinensis* (Jojoba) Seed Oil, *Helianthus Annuus* (Sunflower) Seed Oil, Tocopherol, *Arnica Montana* Flower Extract, *Glycine Soja* (Soybean) Oil, *Glycine Soja* (Soybean) Oil, *Calendula Officinalis* Flower Extract, Tocopherol, *Hippophae Rhamnoides* (Seabuckthorn) Fruit Oil, C12-C13 Pareth-4, Parfum (Fragrance) and *Dunaliella salina* Extract.

It is another object of the present invention to provide a preparation where said preparation is formulated as a pharmaceutically acceptable Baby scalp oil.

It is another object of the present invention to provide a skin care preparation for babies, comprising: *Vitis Vinifera* (Grape) Seed Oil, *Simmondsia Chinensis* (Jojoba) Seed Oil, *Prunus Amygdalus Dulcis* (Sweet Almond) Oil, *Olea Europaea* (Olive) Husk Oil, *Glycine Soja* (Soybean) Oil, *Calendula Officinalis* Flower Extract, Tocopherol, *Arnica Montana* Flower Extract, C12-C13 Pareth-4, Parfum (Fragrance) and *Dunaliella Salina* Extract.

It is another object of the present invention to provide a preparation where said preparation is formulated as a pharmaceutically acceptable Baby Oil.

It is another object of the present invention to provide a preparation where said preparation contains at least 2% concentration of said *Dunaliella salina* extract.

It is another object of the present invention to provide a preparation where said preparation contains at least 2% concentration of said "SEPITONIC™-M3".

It is an object of the present invention to provide a method for producing a skin care preparation for babies, comprising the steps of: a. providing ingredients selected from the group consisting of: pharma grade water; at least one stabilizer; at least one nutrient; at least one emulsifier; b. weighing each of said ingredients as explained in a protocol; c. adding into a first reactor ingredients belonging to group A; d. mixing until uniform; e. heating to 70 degrees Celsius and mixing until uniform for about 30 minutes; f. adding into a second reactor ingredients belonging to group B; g. heating to 70 degrees Celsius and mixing until uniform for about 30 minutes; h. adding mix of said group B into mix of said group A; i. cooling to 50 degrees Celsius while stiffing and adding the rest of the ingredients; j. mixing and cooling to 25 degrees Celsius; wherein said step of providing ingredients further comprises a step of providing Zinc gluconate & magnesium asparate & copper gluconate ("SEPITONIC™-M3") and *Dunaliella salina* extract.

It is another object of the present invention to provide a method where said at least one stabilizer is selected from a group consisting of: Stearic acid; *Butyrospermum parkii* (shea butter); *Cera alba* (beeswax); Glycerin; Phenoxyethanol; Sodium hydroxide; Carbomer (benzene free); Perfume 187722 creme soap; *Chamomilla recutita (matricaria)* extract, Sodium chloride; Citric acid; Zinc oxide (ci 77947); Caprylic/capric triglyceride; Hydroxypropyl Guar Hydroxypropyltrimonum Chloride; Ethylhexylglycerin; and any combination thereof.

It is another object of the present invention to provide a method where said at least one nutrient is selected from a group consisting of Panthenol; Tocopheryl acetate; *Olea europaea* (olive) fruit oil; Aloe barbadensis (aloe vera leaf juice); Allantoin; Sodium Cocoamphoacetate; Disodium Laureth Sulfosuccinate; Aloe Barbadensis Leaf Juice; Zinc oxide (ci 77947); *Ricinus communis* (castor) seed oil; Panthenol; Gluconolactone & sodium benzoate & calcium gluconate; Aqua & sodium lactate & sodium pca & glycine & fructose & urea & niacinamide & inositol & sodium; Benzoate; and any combination thereof.

It is another object of the present invention to provide a method where said at least one emulsifier is selected from a group consisting of Stearic acid; *Butyrospermum parkii* (shea butter); Dimethicone; Cetearyl alcohol; Glycerin; Panthenol; *Olea europaea* (olive) fruit oil; Carbomer (benzene free); Sodium Cocoamphoacetate; Disodium Laureth Sulfosuccinate; *Chamomilla Recutita* Flower Water; *Olea europaea* (olive) Husk oil; Ethylhexylglycerin; Cetearyl alcohol & peg-20 stearate; *Ricinus communis* (castor) seed oil; Caprylic/capric triglyceride; Polysorbate 60; Dimethicone; *Calendula officinalis* flower extract (marigold oil); Magnesium laureth sulfate & disodium laureth sulfosuccinate; Cocamidopropyl betaine & aqua; and any combination thereof.

It is another object of the present invention to provide a method where said group A comprise ingredients selected from the consisting of: Aqua (water), Stearic acid, *Butyrospermum parkii* (shea butter), Dimethicone, *Cera alba* (beeswax), Cetearyl alcohol, Glycerin, Panthenol, Tocopheryl acetate, *Olea europaea* (olive) fruit oil, Aloe barbadensis (aloe vera leaf juice), Phenoxyethanol, Allantoin, Sodium hydroxide, Carbomer (benzene free), Perfume 187722 creme soap, Zinc gluconate & magnesium asparate & copper gluconate, *Dunaliella salina* extract, Sodium Cocoamphoacetate, Disodium Laureth Sulfosuccinate, *Chamomilla Recutita* Flower Water, *Olea europaea* (olive) Husk oil, Hydroxypropyl Guar, Hydroxypropyltrimonum Chloride, Ethylhexylglycerin, Citric Acid Cetearyl alcohol & peg-20 stearate, Zinc oxide (ci 77947), *Ricinus communis* (castor) seed oil, Caprylic/capric triglyceride, Polysorbate 60, *Calendula officinalis* flower extract (marigold oil), Gluconolactone & sodium benzoate & calcium gluconate, Magnesium laureth sulfate & disodium laureth sulfosuccinate, Cocamidopropyl betaine & aqua, *Chamomilla recutita* (*matricaria*) extract, Aqua & sodium lactate & sodium pca & glycine & fructose & urea & niacinamide & inositol & sodium, Benzoate, Sodium chloride, *Persea Gratissima* Avocado Oil, *Simmondsia Chinensis* (Jojoba) Seed Oil, *Helianthus Annuus* (Sunflower) Seed Oil, *Arnica Montana* Flower Extract, *Glycine Soja* (Soybean) Oil, *Hippophae Rhamnoides* (Seabuckthorn) Fruit Oil, C12-C13 Pareth-4, Parfum (Fragrance), *Vitis Vinifera* (Grape) Seed Oil, *Prunus* Amygdalus Dulcis (Sweet Almond) Oil, and any combination thereof.

It is another object of the present invention to provide a method where said group B comprise ingredients selected from the consisting of: Aqua (water), Stearic acid, *Butyrospermum parkii* (shea butter), Dimethicone, *Cera alba* (beeswax), Cetearyl alcohol, Glycerin, Panthenol, Tocopheryl acetate, *Olea europaea* (olive) fruit oil, Aloe barbadensis (aloe vera leaf juice), Phenoxyethanol, Allantoin, Sodium hydroxide, Carbomer (benzene free), Perfume 187722 creme soap, Zinc gluconate & magnesium asparate & copper gluconate, *Dunaliella salina* extract, Sodium Cocoamphoacetate, Disodium Laureth Sulfosuccinate, *Chamomilla Recutita* Flower Water, *Olea europaea* (olive) Husk oil, Hydroxypropyl Guar, Hydroxypropyltrimonum Chloride, Ethylhexylglycerin, Citric Acid Cetearyl alcohol & peg-20 stearate, Zinc oxide (ci 77947), *Ricinus communis* (castor) seed oil, Caprylic/capric triglyceride, Polysorbate 60, *Calendula officinalis* flower extract (marigold oil), Gluconolactone & sodium benzoate & calcium gluconate, Magnesium laureth sulfate & disodium laureth sulfosuccinate, Cocamidopropyl betaine & aqua, *Chamomilla recutita* (*matricaria*) extract, Aqua & sodium lactate & sodium pca & glycine & fructose & urea & niacinamide & inositol & sodium, Benzoate, Sodium chloride, *Persea Gratissima* Avocado Oil, *Simmondsia Chinensis* (Jojoba) Seed Oil, *Helianthus Annuus* (Sunflower) Seed Oil, *Arnica Montana* Flower Extract, *Glycine Soja* (Soybean) Oil, *Hippophae Rhamnoides* (Seabuckthorn) Fruit Oil, C12-C13 Pareth-4, Parfum (Fragrance), *Vitis Vinifera* (Grape) Seed Oil, *Prunus* Amygdalus Dulcis (Sweet Almond) Oil, and any combination thereof.

It is another object of the present invention to provide a method where said preparation contains at least 2% concentration of said *Dunaliella salina* extract.

It is another object of the present invention to provide a method where said preparation contains at least 2% concentration of said "SEPITONIC™-M3".

It is another object of the present invention to provide a method where said preparation is formulated as a pharmaceutically acceptable Baby lotion.

It is another object of the present invention to provide a method where said preparation is formulated as a pharmaceutically acceptable Baby cleansing mousse.

It is another object of the present invention to provide a method where said preparation is formulated as a pharmaceutically acceptable Dipper rash cream.

It is another object of the present invention to provide a method where said preparation is formulated as a pharmaceutically acceptable Tearless Baby Shampoo.

DETAIL DESCRIPTION OF THE PREFERRED EMBODIMENTS

The following description is provided, so as to enable any person skilled in the art to make use of the invention and sets forth the best modes contemplated by the inventor of carrying out this invention. Various modifications, however, are adapted to remain apparent to those skilled in the art, since the generic principles of the present invention have been defined specifically to provide a skin care preparation for babies. Thus a novel method for creating such preparation has been obtained.

When babies are born, they emerge from the womb's sterile environment into a world filled with bacteria, pollution, humidity and heat, solar radiation, etc. Baby's skin excels in its ability to adapt to the environment. This ability improves gradually over the first years of life, in general, and during the first year, in particular. This period is marked by adaptation to human contact and to open air, at home and outside. Together with this, the baby's diet (either mother's milk or formula) are filled with hormones which often intensify the activity of sebaceous glands, etc.

During this adaptation period, a large percentage of babies suffer from various skin disorders. Recognizing and taking care of them is essential for easy, quick and "painless" adaptation.

During the first months of life, the baby's skin is thinner and more delicate than that of adults, and is more susceptible to irritation and pollution. Moreover, the skin's moisture regulating mechanism develops gradually and baby's skin becomes dry relatively quickly. Perspiration glands are also in the process of developing and, as a result, it is difficult regulate both skin temperature and sebaceous gland secretion.

The present invention was developed taking into account baby's adaptation to environmental factors. The series contains ingredients which are designed to soothe skin stress (Aloe Vera, Chamomile, Panthenol, Jojoba Oil), support immune system functioning (*Dunaliella Salina* extract, Sepitonic M3, Chamomile, *Arnica* Extract, Olive Oil, Beeswax), balance the skin's moisture level (herbal glycerin, aloe vera, jojoba oil, shea butter, *calendula* extract), and creates a protective environment which strengthens the epidermis (*Dunaliella Salina* extract, Sepitonic M3, Vitamin E, Apple Amino Acids, Olive Oil).

The present invention supports optimal natural dermal adaptation processes and provide tools for effective, easy to use, skin relief and protection.

Several factor must be taken under consideration:
1. Skin Acidity—Up to the age of 6 months, the pH of babies' skin is neutral since the skin's protective acid mantle has not yet fully developed. The pH of the acid mantle which usually develops after the age of 6 months is usually lower than 4 and serves as a protective layer against bacteria and other microorganisms which find it difficult to inflict damage at this low pH level. The acid mantle helps to preserve moisture and elasticity which typifies children's skin until around the age of 10.

In order to support baby's delicate skin during the first months of their lives, we developed products which, on the one hand, support the acid pH level while, on the other, provide moisture and create a stress-free skin environment to bolster the developing dermal immune system in its "battle" against environmental aggressors.

2. Skin Thickness—Baby's skin is thinner and more delicate than that of adults. It has very few perspiration glands and, therefore, it is difficult to regulate skin temperature. Baby's skin tends to becomes dry and moisture levels are not properly balanced. Given the above, baby's skin is more ideally suited to the womb than to an external environment which requires thicker skin. Thin, delicate skin is more vulnerable to irritation and inflammation and is missing a protective layer.

Therefore, the present invention combine ingredients which add moisture and preserve it in the epidermis, protective ingredients which help form the acid mantle to guard against the harmful activity of bacteria and other microorganisms, ingredients which help strengthen the skin's immune system and skin soothers to de-sensitize the delicate, sensitive skin which is one of the body's major tactile organs.

3. Skin Hormone Levels—There are a number of manifestations of elevated hormone levels in skin: bloody secretions in girls (the result of hormones passed on through the placenta), swelling of the breasts and/or scrotum, dark spots on the baby's bottom—which are either excess pigmentation or residue from a layer which covered the baby's skin and has remained mostly in the folds of the neck, groin and underarms (particularly in babies who were born after week 40).

These phenomena usually disappear by themselves and require no special treatment.

In view of the above, care of baby's skin requires mainly prevention and support. In terms of prevention—the present invention help skin attain balance by strengthening natural process and help form the acid mantle. This prevention is the result of daily hygiene:
1. Maintaining proper skin temperature (not exposing the baby to extreme heat which can cause redness, irritation, pimples and itchiness and increased bacterial activity. On the other, it is imperative not to expose the baby's skin to extreme cold which can reduce body temperatures, weaken the skin's immune system and cause bacterial and other harmful activity).
2. Exposing skin to open air—Make sure the diaper area is exposed to open air as much as possible, making sure it is not completely sealed for long stretches of time. It is important to suit clothing to weather conditions. Applying baby-suitable sunscreens should be part of the daily skin care regimen.
3. Bathing—Bathing too often will damage the skin's protective layer; if bathing isn't frequent enough, skin cells will not regenerate properly.
4. After bathing, pat dry baby's skin using a soft towel to avoid damaging the baby's delicate skin while at the same time making sure that no areas are left damp—these can become the source for unpleasant skin disorders (itchiness, redness, pimples, etc.).
5. Sleep—While sleeping, baby's bodies strive to achieve balance, including the developing skin. When baby's sleep, the skin receives most of the nutrients it needs to grow properly. Therefore, sleep as an essential building block of healthy skin.
6. Nutrition—We suggest to gradually expose babies to new foods—making sure that urine, feces and perspiration fluid are lightly colored and are as frequent as defined by health authorities all over the world. Proper draining of the body's systems directly impacts the proper development of skin systems for healthier skin.

The present invention offers two stages of baby skin care.
Stage 1— daily skin care for newborns
Stage 2— skin care for older babies The products of the present invention provide pleasant, skin-friendly maintenance—without harmful deodorants (SLS and SLES free), containing skin-friendly preservatives (paraben-free), with natural oils and extracts and the Dead Sea algae known for its skin soothing and protective properties. A few examples may include:
1. Tearless Shampoo—Contains ingredients which enhances skin moisture levels for up to 8 hours even after the baby has been "washed and dried".
2. Baby Lotion— A gentle lotion, quickly absorbed. A measured amount of "Baby Lotion" is enough to soothe skin, but will keep the baby from slipping.
3. Diaper Rash Cream—Absorbs liquids, soothes skin and helps prevent irritation. Provides a protective barrier between baby's delicate skin and body secretions.

The second stage of the products of the present invention may be:
Cleansing Mousse
Baby Bath Oil Forte
Diaper Rash Forte
Mosquito Repellant
Ultra Gel
Environmental Protection Spray These address the same parameters referred to above: prevent skin stress, bolster the skin's immune system, add and preserve moisture, and maintain an intact epidermal barrier.

All products have been dermatologically tested and have been assessed as safe by independent Safety Assessors.

In one embodiment the present invention includes two unique complexes which serve as a breakthrough in baby skin care:
"Dusu Complex".
"Duse Complex".

These complexes are based on the benefits of the Dead Sea Alga—"*Dunaliella Salina*" in Dermo-Cosmetically care specifically accommodating the baby's delicate skin.
1. The "Dusu" Complex incorporates the advantages of the Dead Sea Alga "*Dunaliella Salina*", which is rich in: Beta Carotene (Vitamin A & Glycerol, known as essential to healthy skin functioning, enriched with moisture).

Assisting in anti-free radical functions and in preventing dryness.

Together with "Sunflower Oil" or "Olive Oil", which is mainly Tri-Glycerides, containing fatty acids 6,9, and is known for its significant ability to sore moisture in the skin. Also as a protective barrier for the baby's skin (according to research) while resisting dirt and harmful environmental influences.

The incorporation of the "*Dunaliella Salina*" alga with "Sunflower Oil" or "Olive Oil" creates a protective complex that resists environmental damage to the skin and supports proper skin functions.

2. The "duse" Complex incorporates the advantages of the Dead Sea "*Dunaliella Salina*" alga with mineral complex "SEPITONIC™-M3", with proven properties that support the energetics of skin cell replacement, while removing toxins and balancing their development.

The integration of "*Dunaliella Salina*" alga with the "SEPITONIC™-M3" mineral complex provides efficient support to the strengthening of the skin's texture and resistance, and to the balanced and natural cellular development.

These advantages, together with the additional ingredients comprising the present invention, provide a pampering, flexible and supportive touch to the baby's skin.

While several ingredients may be used in the manufacturing of the products of the present invention, here are some of the most used ingredients and their role in the preparations:

*Dunaliella Salina* Oil: *Dunaliella salina* belongs to the Chlorophyceae. It is considered that this uni-cellular alga, like 25 other species of Chlorophyceae which are classified as food sources, does not produce toxins. Acute toxicity: LD50 of a preparation containing 30% of beta-carotene is higher than 20 g/kg b/w. in the mouse. Short-term toxicity: several studies have been conducted during 2 to 8 weeks on rat and chicken with a powder of the alga *Dunaliella bardawil* which the Committee has been informed is identical to the species *Dunaliella salina*, without signs of toxicity up to the equivalent of 0.1% of beta-carotene in the diet. Multigeneration reproduction study: no toxicity has been assigned to a powder of *Dunaliella bardawil* ingested by the rat up to 10% in the diet (equivalent to 0.2% of beta-carotene). Genotoxicity: the algal beta-carotene was unable to induce gene mutation or chromosomal aberrations in two Ames tests and one chromosome aberration assay in human lymphocytes. Data obtained on the algal powder provide reassurance of the absence of toxicity of the components other than beta-carotene. This is important for the safety evaluation of the beta-carotene preparation in the absence of a total crystallization of beta-carotene. Skin contact: it is not expected to produce any toxic reaction (irritation, sensitization) when *Dunaliella Salina* Oil applied topically. (Ref: EC Scientific Committee on Food—Opinion On A Request For The Use Of Algal Beta-Carotene As A Food Color (Expressed On 13 Jun. 1997)). It is a natural source of antioxidants, carotenoids, vitamins, minerals, amino acids, polysaccharides, essential fatty acids, chlorophyll and phytonutrients. Role: Helps maintain healthy skin; Improves protection against UV radiation; Contributes to healthy skin functioning; and Helps revitalize skin.

*Vitis Vinifera* (Grape) Seed Oil: Grape seed oil (also called grapeseed oil or grape oil) is a vegetable oil pressed from the seeds of various varieties of *Vitis vinifera* grapes, an abundant by-product of winemaking. It is an emollient oil that reduces TEWL and represents no hazard to the skin when applied topically. Function: Emollient. Moisturizer and anti-oxidant. Supports skin repair. Contains polyphenols and flavonoids—strong antioxidant compounds. The actual or estimated LD50 value: 5,000 mg/kg body weight. Comedogenic value: 2.5 (one researcher found a value of 2 and another 3).

*Simmondsia Chinensis* (Jojoba) Seed Oil/Extract: *Simmondsia Chinensis* Seed Extract is an extract of the seeds of the Jojoba, *Simmondsia chinensis*, Buxaceae. Function: A natural emollient, jojoba oil's similarity to sebum allows it to be absorbed easily and readily into your skin, making it a gentle, skin-softening moisturizer for all skin types. Anti-oxidant. Forms a semi-occlusive epidermal barrier keeping moisture in while letting skin breathe. Non-greasy. Active bacteria neutralizer. Moisturizes and elasticizes skin. Soothes skin and stimulates skin repair. The actual or estimated LD50 value: 7500 mg/kg body weight. Oral LD50 value (rat): 5,000 mg/kg.

*Prunus* Amygdalus *Dulcis* (Sweet Almond) Oil: Function: Emollient/skin conditioning. Highly effective cleanser—removes dirt and impurities. Helps remove dead cells and lets skin breathe. Contains powerful anti-oxidants. Moisturizes, nourishes and protects skin. The actual or estimated LD50 value: 115,000 mg/kg body weight. Oral LD50 value (rat): 5,000 mg/kg. Dermal LD50 value (rabbit): 5,000 mg/kg. Comedogenic value: 1-3. *Prunus* Amygdalus *Dulcis* (Sweet Almond) Oil. CIR: Maximum "as used" concentration for safe as used conclusion: up to 76%.

*Olea Europaea* (Olive) Husk Oil: Cosmetics Functions: Emollient/Perfuming/Solvent/Fragrance Ingredient/Skin Conditioning agent-Occlusive. *Olea Europaea* Fruit Oil is the fixed oil obtained from the ripe fruit of the olive tree, *Olea europaea*, Oleaceae (Ph. Eur. Name: Olivae oleum). It consists primarily of the glycerides of the fatty acids linoleic, oleic and palmitic. That is, a mix of saturated and polyunsaturated fatty glyceryl esters (namely, mixed glycerides comprising oleic acid at 83.5%, palmitic acid at 9.4%, linoleic acid at 4%, stearic acid at 2% and arachidc acid at 0.9% along with other constituents such as squalene at up to 0.7%, phytosterol at 0.2%, tocopherol (0.2%) and phenolic compounds (The Merck Index values cited by Beukers S M et al. 2008. Cheilitis due to olive oil. Contact Dermatitis, 59, 253-255). Olive oil is used in a range of pharmaceutical topical ointments/creams and cosmetic products. It can also be used as vehicle to identify allergens in patch testing (Beukers S M et al. 2008). The effect of olive oil on babies' skin has been equated with the observation made in adults with low skin barrier such as the case with eczematous skin. Babies and particularly newborn have very thin stratum corneum (skin barrier) (Nikolovski et al, J Invest Dermatol., 128, 2008). The epidermis of newborn babies has been demonstrated to be 20% thinner and the stratum corneum 30% thinner than an adult skin (cited by Crozier, K and Macdonald S, 2010 in Evidence Based Midwifery 8(4): 128-135). An important organizational component of human skin at the molecular level is Ceramide 1. Constituent of oilve oil, oleic acid (83.5%) has been associated with the disruption of Ceramide 1 and subsequently the skin barrier thus enabling trafficking of chemicals that would normally not gain access into the skin. In contrast to Oleic acid, the other constituent of olive oil, Linoleic acid linearly and neatly integrates with Ceramide 1 skin structure. It is thus suggested that natural oils that are rich in Linoleic acid and low in Oleic acid (such as Sunflower oil) are less likely to interfere with the skin structure where topical products are intended for application on babies. It soothes, smoothes and nourishes skin. Anti-oxidant protection. Helps protect against damage caused by ultraviolet light. Moisturizes and elasticizes. Calms redness and irritation. Enriched with Vitamin E—Anti-oxidant, helps protect against free-radical damage.

*Glycine Soja* (Soybean) Oil: This plant has been known and used by the Chinese for more than 4,000 years, though today most of the oil comes from the USA. This oil is a cost-effective base on which to prepare hair and body products where good honest moisturization is required at a budget price. Soybean is listed as a major starting material for stigmasterol, once known as an anti-stiffness factor. Sitosterol, also a soy byproduct, has been used to replace diosgenin in some antihypertensive drugs. Function: Emollient/skin conditioner. The actual or estimated LD50 value: 50,000 mg/kg body weight. Comedogenic value: 3.

*Calendula Officinalis* Flower Extract: The Food and Drug Administration (FDA) includes *Calendula officinalis* on its list of substances considered Generally Recognized As Safe (GRAS) as a spice and natural seasoning/flavoring. The safety of *Calendula Officinalis* Extract, *Calendula Officinalis* Flower, *Calendula Officinalis* Flower Extract, *Calendula Officinalis* Flower Oil and *Calendula Officinalis* Seed Oil has been assessed by the Cosmetic Ingredient Review (CIR) Expert Panel. The CIR Expert Panel evaluated scientific data and concluded that the *Calendula*-derived ingredients are safe as used in cosmetics and personal care products. Function: Emollient, contains high levels of carotenoids (vitamin-A like compounds) to help soothe and calm redness and irritation. Helps accelerate skin repair processes and restoration. Contributes to neutralizing bacterial activity. The actual or estimated LD50 value: 2,000 mg/kg body weight. CIR: Maximum "as used" concentration for safe as used conclusion: up to 6%.

Tocopherol: LD50 (oral): Tocopherol: >4,000 mg/kg (rat) >25 ml/kg (mouse); LD50 (dermal): Tocopherol: >3,000 mg/kg (rat). The Food and Drug Administration (FDA) includes Tocopherol on its list of nutrients considered Generally Recognized As Safe (GRAS). Tocopherol is also on FDA's list of GRAS food preservatives. The safety of Tocopherol and related ingredients (Dioleyl Tocopheryl Methylsilanol, Potassium Ascorbyl Tocopheryl Phosphate, Tocophersolan, Tocopheryl Acetate, Tocopheryl Linoleate, Tocopheryl Linoleate/Oleate, Tocopheryl Nicotinate, Tocopheryl Succinate) has been assessed by the Cosmetic Ingredient Review (CIR) Expert Panel. The CIR Expert Panel evaluated the scientific data and concluded that Tocopherol and the related ingredients were safe as used in cosmetics and personal care products. Function: Antioxidant/skin conditioning. The actual or estimated LD50 value: 7000 mg/kg body weight. Oral LD50 value (rat): 5,000 and 9,000 mg/kg; (mouse): 50,000 mg/kg. Comedogenic value: 0. Tocopherol. CIR: Maximum "as used" concentration for safe as used conclusion: </=5%.

*Arnica Montana* Flower Extract: *Arnica Montana* Extract was reported to be used in almost 100 cosmetic formulations across a wide range of product types, whereas *Arnica Montana* was reported only once. Function: Tonic/emollient/antidandruff/antimicrobial. The actual or estimated LD50 value: 2,500 mg/kg body weight. Oral LD50 value (rat): 650 and 3,000 mg/kg.

C12-C13 Pareth-4: The safety of ingredient was assess by CIR. The CIR Expert Panel concluded that the alkyl PEG ethers (including C12-13 Pareth-4), listed below, are safe in the present practices of use and concentration described in safety assessment when formulated to be non-irritating. Function: Emulsifying/surfactant. The actual or estimated LD50 value: 2,000 mg/kg body weight.

Parfum (Fragrance): Fragrance allergens must be calculated and compared to the limits imposed by the IFRA QRA category for the product. All values should fall below the IFRA limit. According to allergen analysis provided no allergen need to be indicated on the label.

Aqua (water): Function: Solvent. Simply water unlikely to cause irritation, allergy or harm. Used in many cosmetic products as a solvent and necessary to sustain biological life. The source of water should be known, monitored to GMP and either a deionized or high purity grade free from toxins, pollutants and bacteriological contamination should be used in cosmetic products.

Stearic acid: Cosmetic Functions: Cleaning/Emulsifying/Emulsion stabilising/Masking/Refatting/Surfactant. This fatty acid has a low potential to irritate the skin. When added as super fatting agent to soap reduces the skin and eye irritancy potential.

*Butyrospermum parkii* (shea butter): Cosmetic Functions: Skin conditioning, viscosity controlling, emulsifying, emulsion stabilizing, surfactant, viscosity controlling agent. Natural repair agent—helps revitalize skin. Increases water binding capacity. A mixture of fatty acid/fatty alcohol esters (triacylglycerol) with low potential to irritate the skin or eye. Fat from the fruit of *Butyrospermum Parkii*, Shea or Shea nut tree. In Africa also used as a food source for dietary fat.

Dimethicone: Cosmetic Functions: film former. Dimethicone is a mixture of fully methylated linear siloxane polymers end blocked with trimethylsiloxy units. This substance is essentially non-irritating to skin and the eye, is not absorbed through the skin and has no potential to cause skin sensitisation.

*Cera alba* (beeswax): Cosmetic Functions: Emollient/Emulsifying/Film Forming/Binder/Emulsion Stabilizer/Epilating agent/Fragrance Ingredient/Skin conditioning agent/Viscosity Increasing agent-non-aqueous. Beeswax has a low potential to irritate the skin or eye.

Cetearyl alcohol: Cosmetic Functions: Emollient/Emulsifying/Emulsion Stabilising/Foam Boosting/Masking/Opacifying/Surfactant/Viscosity Controlling. A mixture of Cetyl and Stearyl Alcohols (known also as Cetostearyl Alcohol or Cetylstearyl Alcohol) from a series of long chain fatty alcohols which are considered to be only slightly toxic at most.

Glycerin: Function: Denaturant/Humectant/Solvent/Conditioner, Viscosity Decreasing Agent. Contributes to skin cell rejuvenation. Skin protector—keeps skin smoother and protects against redness and disorders caused by over-dry skin. Nourishes and refreshes skin.

Panthenol: Cosmetic Functions: (Pro-vitamin B5)—Helps relieve skin redness, stimulates skin repair. Soothes and moisturizes skin Antistatic/Hair & Skin Conditioning. Widely used in cosmetics. Low toxicity, unlikely to cause problems in normal use. The alcohol analogue of panthenoic acid (Vitamin B3).

Tocopheryl acetate: Cosmetic Function: Antioxidant/Skin Conditioning. Tocopheryl acetate is the ester of Tocopherol (q.v.) and acetic acid. The basic mode of action of tocopherols in human tissue is to prevent the oxidation of polyunsaturated fatty acids (PUFA) by trapping free radicals and donating hydrogen. It is effective in protecting the integrity of lipid and phospholipid in membranes and thus the requirement for vitamin E and the recommended intake is determined to a large extent by the intake of PUFAs. In human metabolism, vitamin E is known to interact with other nutrients which are also involved in the pathways of oxidation processes. Vitamin C, selenium and zinc interact synergistically with vitamin E. Conversely, an iron overload is associated with a lowering of serum vitamin E levels (SCF, 2003). In vivo and in vitro studies suggest that the rate of uptake of vitamin E is controlled by passive diffusion. Absorption of tocopherols (vitamin E) is incomplete; the extent of oral absorption is dependent on intake and varies between 20-80%. The proportion absorbed decreases with increasing amount added to experimental diets; the average absorption is about 40-60% while pharmacological doses of 200 mg and more are absorbed to the extent of <10%. Cannulation studies indicate that there is no difference in absorption between α-tocopherol and α-tocopheryl acetate at physiological doses. At high levels of intake, (>400 IU/day) a higher degree of absorption was obtained with free tocopherol than tocopheryl esters. About 90% of the free α-tocopherol is transported via the lymphatic system into the bloodstream, where it is distributed into lipoproteins on passage into the liver. Excess intake of tocopherol results mostly in the conversion to water-soluble lactone, esterification to glucuronic acid, and excretion in the urine. The endogenous concentration of tocopherol in the skin is approximately 1.0 nmol/g. Blood concentrations in healthy adults, children, infants, and premature infants are approximately 1, 0.8, 0.4, and 0.24 mg/dl, respectively.

Aloe barbadensis (aloe vera leaf juice): Cosmetic functions: Skin Conditioning. A widely used cosmetics ingredient. Low potential to cause skin or eye irritancy. Purified to remove possible allergenic materials. Aloe-derived material has fungicidal, antimicrobial, and antiviral activity, and has been effective in wound healing and infection treatment in animals. It is a powerful moisturizer and skin soother.

Phenoxyethanol: Cosmetic Functions: Preservative/Fragrance Ingredient. A widely-used and well-accepted preservative.

Allantoin: Cosmetic functions: Skin Conditioning/Skin Protecting/Soothing. Powerful hydratant. Calms and balances skin functioning. Protects, revitalizes, soothes and smoothes. Low acute toxicity and minimal potential to irritate the skin and eyes, not a skin sensitizer.

Sodium hydroxide: Cosmetic Functions: Buffering/Denaturant. Normally used to neutralize a product so is rarely present as sodium hydroxide if all of the sodium hydroxide is consumed during the reaction Carbomer (benzene free): Cosmetic Functions: Emulsion Stabilizing/Gel Forming/Viscosity Controlling/Viscosity Increasing Agent-Aqueous. A polymeric thickening agent also used as film formers and binding agents. Polyacrylic acids have a low potential to cause irritation or allergy.

Perfume 187722 creme soap: Function: Perfume.

Sepitonic M3—Zinc gluconate & magnesium asparate & copper gluconate: Blue to grey clear liquid used mainly as a skin conditioning/protecting agent. Energizes skin, improves cell metabolism, and stimulates cell regeneration. Protects against free radical damage. Invigorates skin functioning. Photo-protection.

Sodium Cocoamphoacetate: Function: Surfactant/foaming/cleansing/hair conditioning. The actual or estimated LD50 value: 14,859 mg/kg body weight. Oral LD50 value (rat): 14,859 mg/kg.

Disodium Laureth Sulfosuccinate: Function: Cleansing/foam boosting/hair conditioning/hydrotrope/skin conditioning/surfactant. The actual or estimated LD50 value: 5,000 mg/kg body weight. Disodium Cocoamphodiacetate. CIR: Maximum "as used" concentration for safe as used conclusion: up to 12%.

*Chamomilla Recutita* Flower Water: Function: Masking. The actual or estimated LD50 value: 5,000 mg/kg body weight. A less potent alternative to using the pure oil, the distillate is described as being useful for any inflamed skin conditions e.g boils, abscesses, cuts. Like the essential oil it is described as emotionally calming and soothing. It is useful for sensitive, dry or red skin conditions such as eczema, and all dry, flaky, itchy skin conditions.

Hydroxypropyl Guar Hydroxypropyltrimonum Chloride: Function: Binding/emulsion stabilising/film forming/viscosity controlling/antistatic. The actual or estimated LD50 value: 2,000 mg/kg body weight.

Ethylhexylglycerin: A natural preservative used as an alternative to parabens that is derived from glycerin and can also be used as a deodorizer and skin conditioner. Ethylhexylglycerin servces as a surfactant and preservant enhancer and acts as a safe preservative in minute amounts. It's a proven preservative-enhancer. Ethylhexylglycerin is a synthetic compound derived from grains and plants and works by reducing interfacial tension on the cellular walls of micro-organisms, promoting their more rapid destruction and a wider spectrum activity. Function: Skin conditioning. The actual or estimated LD50 value: 2,000 mg/kg body weight. Oral LD50 value (rat): 2,000 mg/kg.

Citric Acid: Cosmetic Function: Buffering/Chelating/pH Adjuster.

Cetearyl alcohol & PEG-20 stearate: Cosmetic Functions: Emollient/Emulsifying/Emulsion Stabilising/Foam Boosting/Humectant/Opacifying/Surfactant/Viscosity Controlling.

Zinc oxide (CI 77947): Cosmetic Functions: Colourant/Bulking/Skin Protecting/UV Absorber. In OTC drug products, it is used as a skin protectant and a sunscreen agent. Practically insoluble in water (0.00016 g/100 ml water), soluble in diluted mineral acids. Zinc Oxide works as a sunscreen agent by reflecting and scattering UV radiation.

*Ricinus communis* (castor) seed oil: Cosmetic Functions: Emollient/Masking/Moisturising/Skin Conditioning/Smoothing/Solvent/Fragrance Ingredient/Skin Conditioning Agent-Occulsive.

Caprylic/capric triglyceride: Cosmetic Functions: Emollient/Masking/Skin Conditioning Agent-Occlusive/Perfuming/Solvent.

Polysorbate 60: Cosmetic Function: Emulsifying/Surfactant. A hydrophilic, nonionic surfactant used in a variety of cosmetic products.

Gluconolactone & sodium benzoate & calcium gluconate: Used as a skin moisturizer.

Magnesium laureth sulfate & disodium laureth sulfosuccinate: Used at low concentration in rinse-off cosmetic products.

Cocamidopropyl betaine & aqua: Cosmetic Functions: Antistatic/Cleansing/Foam Boosting/Hair Conditioning/Surfactant/Viscosity Controlling. An amphoteric surfactant.

Aqua & sodium lactate & sodium pea & glycine & fructose & urea & niacinamide & inositol & sodium benzoate: The product is an aqueous solution of a sugar with a mixture of amino acids plus added partially neutralized lactic acid and sodium PCA. Has skin conditioning properties and will help the removal of dead cells from the surface of the skin. When present in a product with a pH of 6 most of the lactic acid will be present as lactate ions. Use of the raw material at up to 4% is unlikely to cause problems in use. Contains sodium benzoate as a preservative.

Sodium chloride: Cosmetic Functions: Viscosity controlling. In cosmetics and personal care products, sodium chloride is used in the formulation of oral hygiene products, shampoos, fragrance, skin, hair, nail, cleansing, suntan, makeup and bath products.

*Persea Gratissima* Avocado Oil: A complex blend of vitamins A and E and other active materials is reported, which increases skin elasticity and encourages healthy skin. Avocado oil is cold-pressed and refined for stable shelf life. Avocado oil has been used in African skin treatments for centuries. This highly therapeutic oil is rich in vitamins A, B1, B2, B5 (Panthothenic acid), vitamins D and E, minerals, protein, lecithin and fatty acids. It is a useful, penetrating nutrient for dry skin and eczema. Avocado oil is said to have healing and regenerating qualities. There are some avocado butters which are not pure isolated fatty acids, but contain hydrogenated avocado oil or other higher melting point materials.

*Simmondsia Chinensis* (Jojoba) Seed Oil: *Simmondsia Chinensis* Seed Extract is an extract of the seeds of the Jojoba, *Simmondsia chinensis*, Buxaceae. Function: Emollient. The actual or estimated LD50 value: 7500 mg/kg body weight. Oral LD50 value (rat): 5,000 mg/kg.

*Helianthus Annuus* (Sunflower) Seed Oil: Function: Skin conditioning. The actual or estimated LD50 value: 5,000 mg/kg body weight.

Propanediol: 1981 Function: Solvent/viscosity controlling.

*Arnica Montana* Flower Extract: Function: Tonic/emollient/antidandruff/antimicrobial. The actual or estimated LD50 value: 2,500 mg/kg body weight. Oral LD50 value (rat): 650 and 3,000 mg/kg.

*Hippophae Rhamnoides* (Seabuckthorn) Fruit Oil: The oil is an excellent source for Vitamin E, Vitamin C, Beta-carotene, unsaturated fatty acids, essential amino acids and flavonoids. Oils from sea-buckthorn seeds and pulp differ considerably in fatty acid composition. While linoleic acid and α-linolenic acid are the major fatty acids in seed oil, sea buckthorn pulp oil contains approximately 65% combined of the monounsaturated fatty acid, palmitoleic acid, and the saturated fatty acid, palmitic acid. Few other vegetable oils contain a similar quantity of these fatty acids. Both the seed and pulp oils are rich in tocopherols, tocotrienols and plant sterols. In addition, the pulp oil contains especially high levels of carotenoids. Currently, cosmetic companies are adding sea-buckthorn oil to anti-aging preparations for skin rejuvenation and accelerated healing properties. It is also being used topically as a natural treatment for eczema, acne rosacea, acne and acne scars, and as a lotion for minimizing stretch marks. Function: Skin protecting. The actual or estimated LD50 value: 10,000 mg/kg body weight.

Example 1: Baby Lotion Formulation

| Chemical name | Conc. |
| --- | --- |
| Aqua (water) | 71 |
| Stearic acid | 3 |
| Butyrospermum parkii (shea butter) | 3 |
| Dimethicone | 3 |
| Cera alba (beeswax) | 2 |
| Cetearyl alcohol | 2 |
| Glycerin | 2 |
| Panthenol | 2 |
| Tocopheryl acetate | 2 |
| Olea europaea (olive) fruit oil | 2 |
| Aloe barbadensis (aloe vera leaf juice) | 2 |
| Phenoxyethanol | 0.5 |

-continued

| Chemical name | Conc. |
| --- | --- |
| Allantoin | 0.5 |
| Sodium hydroxide | 0.4 |
| Carbomer (benzene free) | 0.4 |
| Perfume 187722 creme soap | 0.2 |
| Zinc gluconate & magnesium asparate & copper gluconate | 2 |
| Dunaliella salina extract | 2 |
| TOTAL | 100 |

Method of Production:
1. Ensure all equipment is clean and disinfected.
2. Weigh all the ingredients.
3. Add into the main reactor—group A (oleic phase). Mix until uniform. Heat to 70 degrees Celsius and mix until uniform for at least 30 minutes.
4. Add into the secondary reactor—group B (hydrophilic phase). Heat to 70 degrees Celsius and mix until uniform for at least 30 minutes.
5. Add group B to group A.
6. Cool to 50 degrees Celsius while stifling and add the rest of the ingredients.
7. Mix and cool to 25 degrees Celsius.
8. Take a sample to QC laboratory
9. Prepare the barrels for the storage of the product in bulk. Make sure the barrels are clean and disinfected before placing cream in barrels.

Example 2: Baby Cleansing Mousse Formulation

| Chemical name | Conc. |
| --- | --- |
| Aqua (water) | 76.49 |
| Sodium Cocoamphoacetate | 10 |
| Disodium Laureth Sulfosuccinate | 3 |
| Zinc gluconate & magnesium asparate & copper gluconate | 2 |
| Dunaliella Salina Extract | 2 |
| Aloe Barbadensis Leaf Juice | 2 |
| Chamomilla Recutita Flower Water | 2 |
| Olea europaea (olive) Husk oil | 1.5 |
| Hydroxypropyl Guar Hydroxypropyltrimonum Chloride | 0.5 |
| Phenoxyethanol, Ethylhexylglycerin | 0.5 |
| Citric Acid | 0.01 |
| TOTAL | 100 |

Method of Production:
1. Ensure all equipment is clean and disinfected.
2. Weigh all the ingredients.
3. Add into the main reactor—group A:
4. Cool to 40 degrees Celsius while stifling and add the rest of the ingredients.
5. Fix to desired pH with Citric acid.
6. Mix and cool to 25 degrees Celsius.
7. Take a sample to QC laboratory
8. Prepare the barrels for the storage of the product in bulk. Make sure the barrels are clean and disinfected before placing cream in barrels.

Example 3: Dipper Rash Cream Formulation

| Chemical name | Conc. |
| --- | --- |
| Aqua (water) | 45.5 |
| Cetearyl alcohol & peg-20 stearate | 18 |
| Zinc oxide (ci 77947) | 8 |
| Ricinus communis (castor) seed oil | 5 |
| Caprylic/capric triglyceride | 5 |
| Glycerin | 2 |
| Polysorbate 60 | 2 |
| Dimethicone | 2 |
| Panthenol | 2 |
| Olea europaea (olive) Fruit oil | 2 |
| Calendula officinalis flower extract (marigold oil) | 2 |
| Tocopheryl acetate | 2 |
| Zinc gluconate & magnesium asparate & copper gluconate | 2 |
| Dunaliella salina extract | 2 |
| Gluconolactone & sodium benzoate & calcium gluconate | 0.5 |
| TOTAL | 100 |

Method of Production:
1. Ensure all equipment is clean and disinfected.
2. Weigh all the ingredients.
3. Add into the main reactor—group A. Mix until uniform. Heat to 70 degrees Celsius and mix until uniform for at least 30 minutes.
4. Add into the secondary reactor—group B. Mix until uniform. Heat to 70 degrees Celsius and mix until uniform for at least 30 minutes.
5. Add group B to group A.
6. Add Zinc Oxide while stiffing.
7. Cool to 50 degrees Celsius while stiffing and add the rest of the ingredients. Mix and cool to 25 degrees Celsius.
8. Take a sample to QC laboratory.
9. Prepare the barrels for the storage of the product in bulk. Make sure the barrels are clean and disinfected before placing cream in barrels.

Example 4: Tearless Baby Shampoo formulation

| Chemical name | Conc. |
| --- | --- |
| Aqua (water) | 40.5 |
| Magnesium laureth sulfate & disodium laureth sulfosuccinate | 25 |
| Cocamidopropyl betaine & aqua | 5 |
| Panthenol | 2.5 |
| Chamomilla recutita (matricaria) extract | 2 |
| Aloe barbadensis (aloe vera leaf juice) | 2 |
| Olea europaea (olive) Fruit oil | 2 |
| Aqua & sodium lactate & sodium pca & glycine & fructose & urea & niacinamide & inositol & sodium Benzoate | 14 |
| Tocopheryl acetate | 2 |
| Zinc gluconate & magnesium asparate & copper gluconate | 2 |
| Dunaliella salina extract | 2 |
| Gluconolactone & sodium benzoate & calcium gluconate | 0.8 |
| Sodium chloride | 0.1 |
| Citric acid | 0.1 |
| TOTAL | 100 |

Method of Production:
1. Ensure all equipment is clean and disinfected.
2. Weigh all the ingredients.
3. Add into the reactor: Water, Geogard Ultra, Cocoamidopropyl Betaine, Magnesium Laureth Sulfate & Disodium Cocoamphodiacetate. Mix until uniform.
4. Heat to 70 degrees Celsius and mix until uniform for at least 30 minutes.
1. Cool to 50 degrees Celsius while stiffing and add the rest of the ingredients.
2. Mix and cool to 25 degrees Celsius.
9. Take a sample to QC laboratory.
10. Prepare the barrels for the storage of the product in bulk. Make sure the barrels are clean and disinfected before placing cream in barrels.

Example 5: Baby Scalp Oil Formulation

| Chemical name | Conc. |
| --- | --- |
| Persea Gratissima Avocado Oil | 40 |
| Simmondsia Chinensis (Jojoba) Seed Oil | 28 |
| Helianthus Annuus (Sunflower) Seed Oil | 21 |
| Tocopherol | 5 |
| Arnica Montana Flower Extract | |
| Glycine Soja (Soybean) Oil | |
| Dunaliella salina oil | 2 |
| Glycine Soja (Soybean) Oil | 2 |
| Calendula Officinalis Flower Extract | |
| Tocopherol | |
| Hippophae Rhamnoides (Seabuckthorn) Fruit Oil | 1 |
| C12-C13 Pareth-4 | 1 |
| Parfum (Fragrance) | 0.2 |
| TOTAL | 100 |

Method of Production:
1. Clean and dry the container and the stainless steel paddle.
2. Make sure all the ingredients are clean and clear.
3. Add all the ingredients abovementioned.
4. Hand-mix for 5 minutes until the preparation is clear.
5. Take a sample to QC laboratory
6. Prepare the barrels for the storage of the product in bulk. Make sure the barrels are clean and disinfected before placing cream in barrels.

Example 6: Baby Oil Forte formulation

| Chemical name | Conc. |
| --- | --- |
| Vitis Vinifera (Grape) Seed Oil | 44.8 |
| Simmondsia Chinensis (Jojoba) Seed Oil | 22.0 |
| Prunus Amygdalus Dulcis (Sweet Almond) Oil | 20.0 |
| Olea Europaea (Olive) Husk Oil | 5.0 |
| Dunaliella Salina Oil | 2.0 |

-continued

| Chemical name | Conc. |
|---|---|
| Glycine Soja (Soybean) Oil | 2.0 |
| Calendula Officinalis Flower Extract | |
| Tocopherol | |
| Tocopherol | 2.0 |
| Arnica Montana Flower Extract | |
| Glycine Soja (Soybean) Oil | |
| C12-C13 Pareth-4 | 2.0 |
| Parfum (Fragrance) | 0.2 |
| TOTAL | 100 |

Method of Production:
1. Clean and dry the container and the stainless steel paddle.
2. Make sure all the ingredients are clean and clear.
3. Add all the ingredients abovementioned.
4. Hand-mix for 5 minutes until the preparation is clear.
5. Take a sample to QC laboratory
6. Prepare the barrels for the storage of the product in bulk. Make sure the barrels are clean and disinfected before placing cream in barrels.

The invention claimed is:
1. A method, comprising:
(a) providing a skin care preparation for babies, comprising:
    pharma grade water;
    at least one stabilizer;
    at least one nutrient;
    at least one emulsifier;
    wherein said preparation further comprises Zinc gluconate & magnesium asparate & copper gluconate and *Dunaliella salina* extract; and
(b) applying said preparation in the form of a tearless baby shampoo, a pharmaceutically acceptable Baby lotion, or a pharmaceutically acceptable Baby cleansing mousse to baby skin that is not inflamed or otherwise irritated.

* * * * *